United States Patent [19]

Hayward et al.

[11] Patent Number: 5,942,501

[45] Date of Patent: *Aug. 24, 1999

[54] CYCLODEXTRIN DERIVATIVE COMPLEX

[75] Inventors: James A. Hayward, Stony Brook; James Maioriello, Huntington; Joseph D. Ceccoli, Farmingville, all of N.Y.

[73] Assignee: Collaborative Laboratories, Inc., East Setauket, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/699,150

[22] Filed: Aug. 16, 1996

[51] Int. Cl.$^6$ .......................... A61K 31/72; A01N 37/36
[52] U.S. Cl. ................................................ 514/58
[58] Field of Search ............................ 514/58, 159, 161, 514/164, 964; 536/103

[56] References Cited

U.S. PATENT DOCUMENTS

| | | | |
|---|---|---|---|
| 2,861,920 | 11/1958 | Dale et al. | 167/65 |
| 4,024,223 | 5/1977 | Noda et al. | 424/180 |
| 4,228,160 | 10/1980 | Szejtli et al. | 424/180 |
| 4,232,009 | 11/1980 | Hayashi et al. | 424/180 |
| 4,351,846 | 9/1982 | Matsumoto et al. | 424/305 |
| 4,352,793 | 10/1982 | Yamahira et al. | 424/180 |
| 4,383,992 | 5/1983 | Lipari | 424/238 |
| 4,407,795 | 10/1983 | Nicolau et al. | 424/180 |
| 4,424,209 | 1/1984 | Tuttle | 424/180 |
| 4,565,807 | 1/1986 | Uekama et al. | 514/58 |
| 4,596,795 | 6/1986 | Pitha | 514/58 |
| 4,710,495 | 12/1987 | Bodor | 514/174 |
| 4,727,064 | 2/1988 | Pitha | 514/58 |
| 4,834,985 | 5/1989 | Elger et al. | 424/488 |
| 4,952,565 | 8/1990 | Zmitek et al. | 514/58 |
| 5,019,563 | 5/1991 | Hunter et al. | 514/58 |
| 5,089,482 | 2/1992 | Hermens et al. | 514/58 |
| 5,180,716 | 1/1993 | Yaksh et al. | 514/58 |
| 5,472,954 | 12/1995 | Loftsson | 514/58 |
| 5,486,508 | 1/1996 | Uda et al. | 514/58 |
| 5,576,311 | 11/1996 | Guy | 514/179 |

FOREIGN PATENT DOCUMENTS 1 222 697   6/1987   Canada .

OTHER PUBLICATIONS

Fenyvesi et al., *Proced. of the Fourth International Symposium on Cyclodextrins*, pp. 227–235, (1988).
Frömming et al. *Arzneim–Forsch.*, 23(3):424–426, (1973).
Nakai et al. *Journal of Incl. Phenomena*, vol. 2: 523–531, (1984).
Szejtli, J. *Medicinal Research Reviews*, vol. 14(3): 353–386, (1994).
Vromans et al. *Acta Pharm. Techol.*, 35(4): 250–4, (1989).
Brewster et al. *J. of Parenteral Sci & Tech*, 43(5): 231–240, (1989).

*Primary Examiner*—Howard C. Lee
*Attorney, Agent, or Firm*—Darby & Darby

[57] ABSTRACT

A salicylic acid (SA) and derivitized beta cyclodextrin complex provides that the SA display increased solubility in water. The complex includes about 0.1 to about 10.0 percent salicylic acid, about 0.1 to about 75.0 percent derivatized beta cyclodextrin and about 0.1 to about 50.0 percent water.

13 Claims, 1 Drawing Sheet

CYCLODEXTRIN DERIVATIVE COMPLEX

BACKGROUND OF THE INVENTION

The present invention relates to cyclodextrin complexes, and more particularly relates to a highly water soluble derivitized beta cyclodextrin complex which contains significant amounts of salicylic acid (SA).

Cyclodextrins are a class of cavity-containing cyclic compounds (oligosaccharides), sometimes described as being donut-shaped, which possess a property of forming special type complexes known as molecular inclusion complexes. Molecular inclusion complexes are molecular compounds which display a characteristic structure of an adduct, that is, they are constructed such that one component (the host) spatially encloses another (the guest), as shown in FIG. 1A. There, an anchored or entrapped guest 1 is typically an active agent, such as a chemical compound, disposed within a cavity 3' of the cyclodextrin molecule 3. The guest's entrapment within the cyclodextrin (complexing agent or host) defines a complex relationship which is devoid of covalent bonds.

The resulting complex may render light and/or oxygen-sensitive material more stable, as well as biologically active substances more controllable. That is, the properties of the host:guest complex may be quite different than those of the host or guest individually. For example, the overall water solubility of the guest may be enhanced relative its water solubility in the uncomplexed state.

Cyclodextrins are synthesized from starch hydrolyzates utilizing transglycosidases. The resulting molecular structure of the cyclodextrins may include from six (6), seven (7), or eight (8) glucopyranose rings, respectively known as ALPHA, BETA, and GAMMA cyclodextrins. An ALPHA cyclodextrin 4 is shown in FIG. 2. Cyclodextrins are water-soluble, a property derived from the location of free hydroxyl groups of each successive glucose unit on "rims" or edges of the donut-shaped cyclodextrin molecules.

FIG. 1B highlights the position of the primary hydroxyl groups, which are located at the outer surface 4 of the ring of cyclodextrin structure 2. The secondary hydroxy groups are located on the opposite edge 6 of the structure. The outer structural portion of the cyclodextrin molecule is substantially hydrophilic, whereas its inner cavity is strongly hydrophobic. Strongly hydrophilic molecules, and strongly hydrated and ionized groups are not, or are only weakly, complexable. Only molecules which are relatively hydrophobic in nature are readily complexable. It follows that the stability of a complex formed is substantially proportional to the hydrophobic character of the guest molecule or moiety, and, concomitantly, well complexable guests are typically poorly soluble in water.

The guest (guests, or portions thereof, depending on the stoichiometry of the complex) is held via non-covalent forces in a form of three distinct spatial bands (or relationships) within the cyclodextrin/active agent complex structure. There are two bands of C—H groups and a band of glycosidic oxygens. The bands form a cooperative array of binding sites which together comprise a relatively non-polar lipophilic micro-environment. Binding facilitated thereby is not fixed or permanent. It is governed by an inherent dynamic equilibrium which is itself dependent upon the geometric and spatial fit of the host/guest molecules, and the solubility of the guest in the medium.

The term, complex stability, refers to a dissociation/association equilibrium of host and guest in solution. Forces (associative/dissociative) interact simultaneously to maintain the complex in its complexed state. Several examples are: hydrophobic interaction forces, Van der Waal forces, London dispersion forces, hydrogen bonding forces, the release of high energy water upon guest inclusion (complexing) and release of conformational strain in a cyclodextrin water adduct.

Complexation can occur either in solution or in the solid state. Heating the solution and/or solid state mixture increases cyclodextrin solubility as well as that of the guest. Those cases in which the guest includes a charged group extending out of the cavity after complexation tend to form soluble complexes. Because different guests typically display varying degrees of solubility in water, and complexation is dependent upon the amount of guests coming into contact with host molecules, organic solvents are sometimes needed to sufficiently dissolve the guest, for example, methanol, ethanol, propanol, etc.

Chemically modified cyclodextrins display physicochemical and inclusion behavior properties which differ from those of unmodified cyclodextrins. Modifying cyclodextrin by adding hydroxy alkyl groups, for example, hydroxypropyl beta cyclodextrin, tends to increase solubility in water to about 60 % or more, which cannot be realized using the unmodified cyclodextrins. FIG. 2 shows the chemical structure of beta (β) cyclodextrins (to be discussed in greater detail below). Similarly, other modified cyclodextrins, such as; quaternary ammonium cyclodextrin, succinylated cyclodextrin, and sulfates cyclodextrin, among others are highly water soluble. These materials are commercially available from American Maize-Products Company, Hammond, Ill.

SUMMARY OF THE INVENTION

The present invention provides a salicylic acid (SA)/derivatized beta cyclodextrin complex which increases the solubility of S.A. in water or mixed aqueous solvent from about 0.3 up to as high as 8 percent. This percentage is calculated based on approximately 10% SA in a derivatized β cyclodextrin, hydroxypropyl β cyclodextrin in particular. The solvent utilized is preferably water, but the invention is not limited thereto. Various compound solvents may be utilized herein, according to one skilled in the art to maintain solubility of guest molecules during complexation. The invention also includes processes for forming same, preferably utilizing hydroxypropyl beta cyclodextrin.

A derivatized beta cyclodextrin/SA complex of this invention includes up to about 10% SA (preferably 5%), up to about 75% derivatized beta cyclodextrin (preferably 60%) and up to about 50% water (preferably 35%). The resulting solution tends to be thick and syrupy at room temperature, but transparent. The complex varies in color from colorless to yellow in accordance with the percentage of SA and the process conditions used to form the complex. The increased solubility essentially enables SA to form a stabilized complex, and remain in solution in amounts far greater than those percentage amounts of solubilized SA presently known.

BRIEF DESCRIPTION OF THE DRAWING FIGURES

DETAILED DESCRIPTION OF THE INVENTION

Figure 1A:
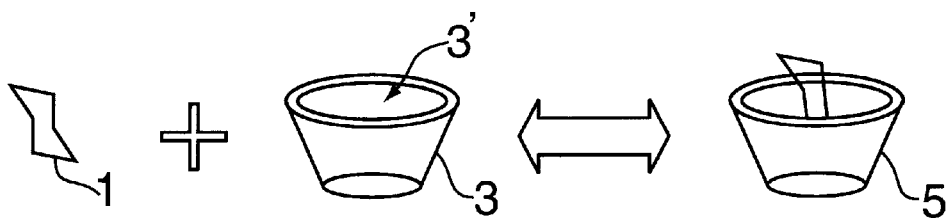
FIG. 1A is a schematic depiction of a cyclodextrin inclusion complex.
Figure 1B:
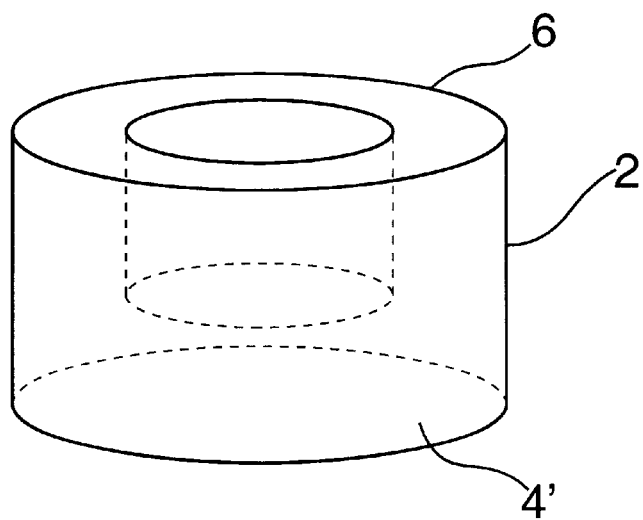
FIG. 1B is a schematic representation of a cyclodextrin structure.
Figure 2:
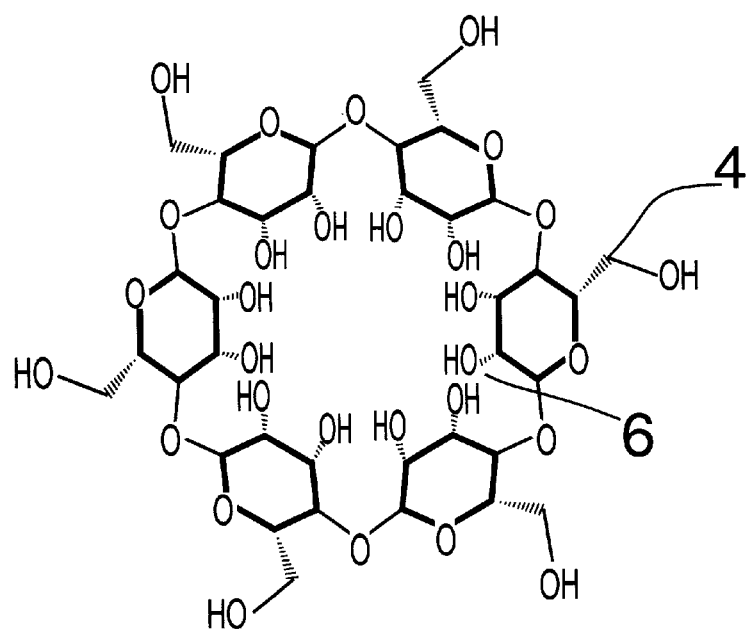
FIG. 2 is a schematic representation of the chemical structure of a cyclodextrin.

Cyclodextrins are enzymatically synthesized starch-ring or donut-shaped molecules which include a substantially central cavity within its structure. Molecular inclusion complexes may be formed utilizing the cyclodextrins unique structure, where one or more guest molecules become stably associated with and held within the cyclodextrin central cavity. While the relationship between the guest molecules and host cyclodextrin molecules may be 1:1, more than one low molecular weight guest may be fit into the cavity of the cyclodextrin molecule. Also, high molecular weight guests may require more than one cyclodextrin molecule to form a complex.

In the case of derivatized cyclodextrins, most of the primary hydroxyl groups, and some of the secondary hydroxyl groups of the outer surface portions of the cyclodextrin molecules, are derivatized in a derivitizing process. These structural changes significantly modify the properties of the native cyclodextrins. Modified beta cyclodextrins, such as hydroxypropyl, hydroxyethyl, methyl or sulfate beta cyclodextrin, when utilized for inclusion complexation, typically display a solubility which in water varies considerably from that of unmodified beta cyclodextrin complexes. In a non-complexed state, ALPHA, BETA and GAMMA cyclodextrins have solubility's in water of 12.7, 1.88 and 25.6 g./ml., respectively, and internal cavities with respective radii of 5.3, 6.5 and 8.3 Angstroms.

The solubility of the complexes formed with unmodified cyclodextrins is considerably higher than the solubility of the guest in the uncomplexed state. Accordingly, cyclodextrins are ideal for applications where the enhanced solubility of the guest molecule is advantageous. For example, cosmetic applications may benefit immensely from the increases availability of SA in solution, as well as in applications such as wart removers and preparations used to treat acne, to name several. This invention provides a way to use modified cyclodextrins to greatly enhance the solubility of a guest complexed with same in a solvent, preferably water, extending the range of the types of formulations which may be used for wart removal, exfoliates, and acne preparations, etc.

In particular, the solubility of salicylic acid in water is about 0.3% at ambient temperatures. Ordinary formulations utilizing salicylic acid, due to its low solubility in water, are typically emulsions, or utilize organic solvents to keep the salicylic acid in solution. A hydroxypropyl-β-cyclodextrin-salicylic acid complex has a solubility in water of greater than 60%. Since the complex, on a solid basis, consists of 10% salicylic acid by weight, salicylic acid is rendered soluble in water to a level of about 6%. This represents a 20-fold increase in the solubility of salicylic acid in water, making it useful for use in wart removers, exfoliates, and acne-preparations where a high level of salicylic acid is required for the effectiveness of the products.

In solution, a complex may exist in a 1:1, 1:2, 2:1 or 2:2 ratio of host to guest. The ratio depends on several properties, such as the size and shape of the guest and the proportions in which they are mixed. The invention described herein, the preferred ratio is 1:1 since this insures the guests are isolated from each other and are contained within the modified cyclodextrin cavity. Various known cyclodextrin (CD) monomers which may facilitate increased solubility of guest complexes include, but are not limited to, hydroxyethyl alpha CD, hydroxyethyl gamma CD, hydroxypropyl alpha CD, sulfated beta CD, sulfated alpha CD, sulfated gamma CD, octenylsuccinylated beta CD, quaternary ammonium alpha CD, quaternary ammonium beta CD, quaternary ammonium gamma CD, quaternary ammonium carboxymethyl beta CD and tertiary amine carboxymethyl beta CD. It should also be mentioned that other materials, such as methyl paraben and phenoxyethanol, as well as many antimicrobial agents are rendered more soluble in complexed form.

In solution, the size and shape of the guest, as well as association/dissociation equilibrium determines the uncomplexed/complexed ratio for guest and host. Depending on properties such as the size and shape of the guest, not only 1:1, but also 1:2, 2:1 and 2:2 host:guest complexes may coexist in solution. Guests are isolated from each other within an oligosaccharide matrix which disintegrates easily under particularized physiological conditions. While pure deionized water is frequently the preferred solvent for use with SA and hydroxypropyl beta cyclodextrin, other solvents or compound solvents may be substituted and/or combined with deionized water. Several examples of other solvent constituents are methanol, ethanol, propanol, etc. In the case of SA, the complex exists in a ratio of 1:1 with the derivatized cyclodextrin.

EXAMPLE 1

Sixty (60) grams of hydroxypropyl beta cyclodextrin were mixed with thirty five (35) grams of deionized water using mechanical stirring at approximately 50 degrees Celsius. Five (5) grams of SA were added to the water/cyclodextrin solution. The solution was stirred until homogeneous. The resulting complex appeared as a thick, clear to yellow fluid-like complex composition or solution. While 50 degrees centigrade is ideal for complex formation, complexation will occur at almost any temperature, the warmer the solution, the faster the complexation will occur.

The preferred process for manufacturing large quantities of the above requires first adding an amount of deionized water equal to approximately 35% of the total weight of the finished product to a mixing container, covering the container and heating same to 50 degrees Centigrade, being careful to avoid overshooting that temperature. An amount of hydroxypropyl beta cyclodextrin equal to approximately 60% of the weight of the final product is then added to the heated water in the mixing container. The mixture is anchored at 20–30 RPM and dispersed at approximately 1200 RPM.

The first 60% of the cyclodextrin may be added to the container in 50 Kg. Portions (of course, depending on the size of the batch), the remainder added in 25 K. portions. The mixing is continued until all the cyclodextrin dissolves. The mixture is then allowed to cool to less than 35 degrees centigrade, to which an amount of Salicylic acid (SA) equal to approximately 35% of the total weight of the final product is added until dissolved, which may be facilitated by mixing at 1200 RPM. Upon dissolution, the disperser is shut down and the mixture allowed to cool to 25 degrees Centigrade. The final product, i.e., the SA/hydroxypropyl beta cyclodextrin complex, is preferably packed through 117 micrometer sieves in sanitary storage means.

As mentioned above, while hydroxypropyl beta cyclodextrin is preferred for SA complexation, various other derivatized beta cyclodextrins may be utilized by those skilled in the art in accordance with the scope and spirit of this invention. For example, hydroxyethyl beta cyclodextrin will complex with SA, phenoxy ethanol, and methyl, ethyl, propyl or butyl paraben, and any other substantially water-insoluble entities such as vitamin A, as is described herein.

EXAMPLE 2

Sixty grams of hydroxyethyl β cyclodextrin was added to 35 grams of deionized water previously heated to between 40 and 60 degrees Celsius. Five (5) grams of salicylic acid were added to the cyclodextrin-water solution. The resulting mixture was stirred until it became homogeneous. The solution appears as a thick, syrupy clear to yellow transparent solution. Alternatively, the guest molecule may be added as a solution in methanol, ethanol, isopropanol, which can be then removed by evaporation.

The foregoing disclosure is merely illustrative of the principles of the present invention and are not to be interpreted in a limiting sense. For example, in Example 2 above, the five grams of SA may be substituted with five (5) grams of phenoxyethanol, or five (5) grams of methyl, or ethyl, or propyl, or butyl paraben. The only limitation on the scope of the invention, therefore, is to be determined from the scope of the appended claims.

What is claimed is:

1. A salicylic acid (SA) and derivatized beta cyclodextrin complex, wherein an amount of SA comprising said complex displays increased solubility in aqueous solution, consisting essentially of in weight percent:

about 0.1 to about 10.0 percent salicylic acid;

about 0.1 to about 75.0 percent derivatized beta cyclodextrin; and about 0.1 to about 50.0 percent water.

2. The SA and derivatized beta cyclodextrin complex defined by claim 1, wherein said stated percent amounts of salicylic acid, derivatized beta cyclodextrin and solvent are about 5, about 60 and about 35 percent, respectively.

3. The SA and derivatized beta cyclodextrin complex defined by claim 1, wherein said derivatized beta cyclodextrin complex includes hydroxypropyl beta cyclodextrin.

4. The SA and derivatized beta cyclodextrin complex defined by claim 1, wherein said water is deionized water.

5. The SA and derivatized beta cyclodextrin complex defined by claim 1, wherein said aqueous solution comprises at least one of the following solvents: methanol, ethanol, isopropanol propanol and deionized water.

6. A method of preparing a salicylic acid (SA) complex in an aqueous solution, wherein SA is present at about 0.1 to about 10.0 percent by weight, derivatized beta cyclodextrin is present at about 0.1 to about 75.0 percent by weight and water is present at about 0.1 to about 50.0 percent by weight and wherein, the SA is maintained solubilized in the aqueous solution in amounts up to seven (7) percent by weight, comprising the steps of:

(a) dissolving said derivatized beta cyclodextrin in heated water to form a cyclodextrin/aqueous solution;

(b) adding SA to said cyclodextrin/aqueous solution to form an SA/cyclodextrin solution;

(c) stirring said SA/cyclodextrin solution;

(d) cooling said SA/cyclodextrin solution such that the SA is maintained solubilized in the solution in amounts up to seven (7) percent by weight while the remainder formed thereby precipitates from said solution; and (e) removing the precipitate.

7. The method of claim 6, wherein the step of collecting said complex includes washing and drying said complex.

8. The method of claim 6, wherein said step of dissolving includes heating said derivatized beta cyclodextrin solution to a temperature within a range of about 0 to about 100 degrees Centigrade.

9. The method of claim 6, wherein said aqueous solution is heated to about 50 degrees Centigrade.

10. The method of claim 6, wherein weight percentages of SA, water and derivatized beta cyclodextrin are about 5, 35 and 60 weight percent, respectively.

11. The method of claim 10, wherein said derivatized beta cylodextrin is hydroxypropyl beta cyclodextrin.

12. The method of claim 10, wherein said percentages of SA, solvent and hydroxypropyl beta cyclodextrin/SA are 5, 35 and 60, respectively.

13. The method of claim 6, wherein said aqueous solution may include at least one of methanol, ethanol, isopropanol and deionized water.

* * * * *

UNITED STATES PATENT AND TRADEMARK OFFICE
Certificate

Patent No. 5,942,501                                                                         Patented: July 20, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James A. Hayward, Stony Brook, NY; James Maioriello, Huntington, NY; Joseph D. Ceccoli, Farmingville, NY; and Mindy S. Goldstein, Ph. D., Plain View, NY.

Signed and Sealed this Twentieth Day of July 2004.

JAMES O. WILSON
*Supervisory Patent Examiner*
*Art Unit 1623*